United States Patent
Gross et al.

(10) Patent No.: US 9,119,774 B2
(45) Date of Patent: Sep. 1, 2015

(54) SELF-HEALING DENTAL RESTORATIVE FORMULATIONS AND RELATED METHODS

(75) Inventors: Stephen M. Gross, Omaha, NE (US); Mark A. Latta, Omaha, NE (US)

(73) Assignee: Premier Dental Products Company, Plymouth Meeting, PA (US)

( * ) Notice: Subject to any disclaimer, the term of this patent is extended or adjusted under 35 U.S.C. 154(b) by 911 days.

(21) Appl. No.: 12/586,233

(22) Filed: Sep. 18, 2009

(65) Prior Publication Data

US 2011/0071234 A1 Mar. 24, 2011

(51) Int. Cl.
*A61K 6/083* (2006.01)
*A61K 6/00* (2006.01)
*A61K 6/09* (2006.01)

(52) U.S. Cl.
CPC ............... *A61K 6/0055* (2013.01); *A61K 6/083* (2013.01); *A61K 6/09* (2013.01); *A61K 6/0047* (2013.01)

(58) Field of Classification Search
CPC ..................................................... A61K 6/0047
USPC .......................................................... 523/116
See application file for complete search history.

(56) References Cited

U.S. PATENT DOCUMENTS

| | | | |
|---|---|---|---|
| 3,505,244 A | 4/1970 | Cessna | |
| 3,704,264 A | 11/1972 | Gorman | |
| 4,221,698 A | 9/1980 | Lee, Jr. et al. | |
| 4,433,958 A | 2/1984 | Fellman et al. | |
| 4,540,723 A | 9/1985 | Ying | |
| 5,192,815 A | 3/1993 | Okada et al. | |
| 6,127,450 A | 10/2000 | Angeletakis | |
| 6,261,360 B1 | 7/2001 | Dry | |
| 6,313,192 B1 * | 11/2001 | Anstice et al. | 523/116 |
| 6,353,040 B1 | 3/2002 | Subelka et al. | |
| 6,444,724 B1 * | 9/2002 | Stangel et al. | 523/116 |
| 6,518,330 B2 | 2/2003 | White et al. | |
| 6,696,507 B2 | 2/2004 | Subelka et al. | |
| 6,730,156 B1 | 5/2004 | Windisch et al. | |
| 6,858,659 B2 | 2/2005 | White et al. | |
| 6,933,361 B2 | 8/2005 | Wudl et al. | |
| 7,569,625 B2 * | 8/2009 | Keller et al. | 523/211 |
| 2004/0097613 A1 * | 5/2004 | Hecht et al. | 523/113 |
| 2005/0250878 A1 | 11/2005 | Moore et al. | |

(Continued)

FOREIGN PATENT DOCUMENTS

JP 2004010529 A * 1/2004 ............. A61K 6/083

OTHER PUBLICATIONS

English machine translation of Okuma (JP 2004-010529); Jul. 17, 2011.*

(Continued)

*Primary Examiner* — Michael Pepitone
(74) *Attorney, Agent, or Firm* — Cozen O'Connor

(57) ABSTRACT

Dental restorative formulations comprising two additives incorporated into the continuous phase of a dental material. One additive contains a capsule with a radical initiator. The other additive contains a capsule with one or more monomers and a radical accelerator. The dental restorative formulation is applied and polymerized to form a composite. When a disturbance occurs in the dental composite, the capsules of the additives rupture so that the radical accelerator of the second capsule decomposes the radical initiator of the first capsule to polymerize the one or more monomers of the second capsule thereby healing the dental composite. The radical accelerator controls the rate of decomposition of the radical initiator.

13 Claims, 1 Drawing Sheet

(56) References Cited

U.S. PATENT DOCUMENTS

| | | | |
|---|---|---|---|
| 2006/0052471 A1* | 3/2006 | Ashman et al. | 522/7 |
| 2006/0111469 A1* | 5/2006 | White et al. | 523/200 |
| 2010/0331445 A1* | 12/2010 | Wilson et al. | 523/116 |
| 2011/0053117 A1* | 3/2011 | Engelbrecht et al. | 433/224 |

OTHER PUBLICATIONS

"Self-Healing Composites Using Embedded Microsphere" D. Jung et al. *Composites and Functionally Graded Materials* vol. MD-80, in the Proceeding of the ASME International Mechanical Engineering Conference and Exposition, 265-275 (1997).

* cited by examiner

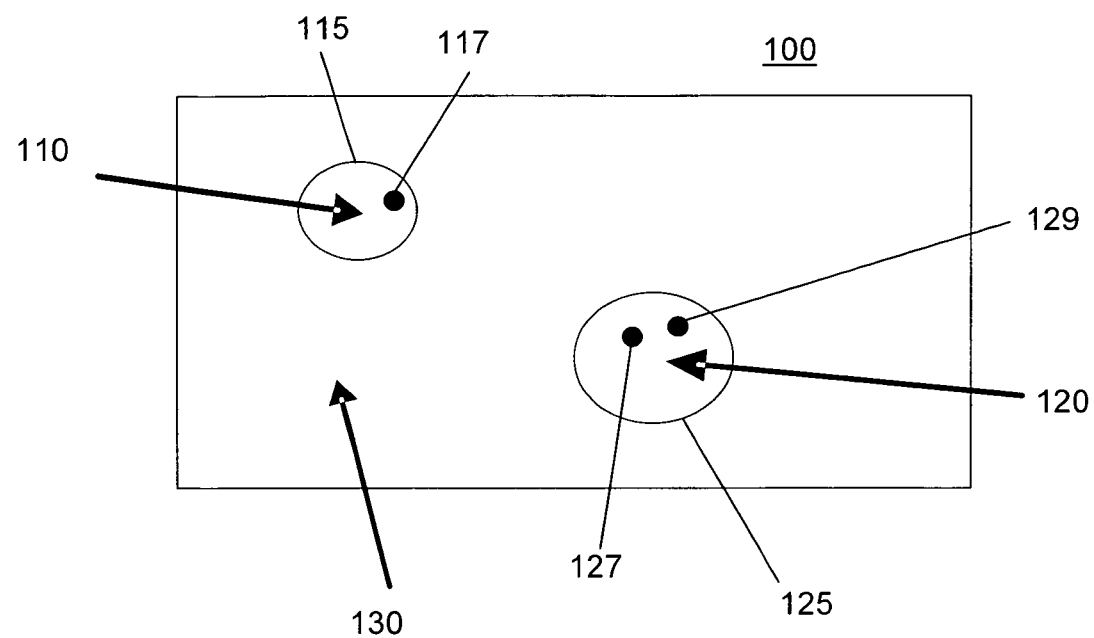

SELF-HEALING DENTAL RESTORATIVE FORMULATIONS AND RELATED METHODS

FIELD OF THE INVENTION

The present invention relates generally to self-healing composites. More specifically, the present invention relates to dental restorative formulations that are applied and polymerized to form self-healing composites with the capability to autonomically resolve disturbances occurring in the composite. The present invention also relates to methods of forming dental restorative formulations. The present invention is useful in a variety of contexts and applications in dentistry including dental repairs, restorations and reconstructions.

BACKGROUND OF THE INVENTION

For purposes of this application, the present invention is discussed in reference to dental applications, but the discussion with respect to dental repair, regeneration or reconstruction is merely exemplary. The present invention is applicable to any context and application that may require self-healing composites.

Dental composites have improved over time. One of the first known dental composites was made with silicate cement. A problem with silicate cement was that it required extreme accuracy during preparation to ensure such a restorative would remain as long as possible. Poorly-made silicate cement restoratives could get destroyed even under the influence of saliva. Another problem with silicate cement was discoloration. Silicate cement absorbs food dyes and tends to yellow over time.

Silicate cement was soon replaced by dental acrylic plastics. Dental acrylic plastics often led to multiple complications, such as pulpitis and periodontitis. Pulpitis is tooth decay that penetrates through the enamel and dentin to reach the pulp of a tooth and periodontitis is any number of inflammatory diseases that affect the tissues surrounding and supporting a tooth. Additionally, acrylic plastics were difficult to polish. Amalgams were an improvement over dental acrylic plastics, but have been shunned by many because of their mercury content.

Metal-based amalgams, then porcelain or other ceramic materials, were used in a variety of remedial dental procedures. Synthetic composites are used as practical alternatives to these materials for such procedures. Synthetic composites typically include a resin with at least one additive to impart a desired property. The composite generally starts out as a paste or liquid and begins to harden when it is activated, either by adding a catalyst, adding water or another solvent, or photoactivation. Advantageously, synthetic composites provide an aesthetically more natural appearance versus porcelain or other ceramic materials.

Synthetic composites are typically made from complex mixtures of multiple components. Synthetic composites must be completely dissolvable in a fluid vehicle, yet remain flowable and viscous; undergo minimal thermal expansion during polymerization; be biocompatible with surrounding surfaces of tooth enamel and colloidal dentin; and, have aesthetic similarity to natural dentition in terms of color tone and polishable texture. Furthermore, synthetic composites must have sufficient mechanical strength and elasticity to withstand ordinary compressive occlusive forces, without abnormal wearing and without causing abrasion to dentinal surfaces.

The different varieties of synthetic composites may be approximately divided into three main groups of products: synthetic resin-based dental composites, glass-based dental composites, and hybrid dental composites.

A synthetic resin-based composite typically comprises materials such as silicate glass or processed ceramic that provides an essential durability to the composite. A synthetic resin-based dental composite typically comprises several monomers combined together. A monomer is a chemical that can be bound as part of a polymer. The synthetic resin-based dental composite includes other materials, such as silicate glass or processed ceramic that provides an essential durability to the composite. These materials may also be made from an inorganic material, consisting of a single type or mixed variety of particulate glass, quartz, or fused silica particles. Using differing types of inorganic materials, with differing diameter sizes or size mixtures, results in differing material characteristics.

Glass-based dental composites are made from glass particles, such as powdered fluoroaluminosilicate, dissolved in an aqueous polyalkenoate acid. An acid/base reaction occurs spontaneously, causing precipitation of a metallic polyalkenoate, which subsequently solidifies gradually. The glass particles may be made from silicate, such as silicone dioxide or aluminum silicate, but may also include an intermixture of barium, borosilicate, alumina, aluminum/calcium, sodium fluoride, zirconium, or other inorganic compounds. Some of the earlier glass-based composites were formulated to contain primarily a mixture of acrylic acid and itaconic acid co-monomers. However, more recently such hybrid products are modified to include other polymerizable components, such as hydroxyethyl methacrylate ("HEMA") or 2,2-bis[4-(2-hydroxy-3-methacryloyloxypropoxy)phenyl]propane ("Bis-GMA").

Hybrid composites are the third category of synthetic composites. Similar to glass-based composites, hybrid composites are typically made from a combination of inorganic compounds and organic compounds, for example, glass particles with one or more polymers. Hybrid composites may comprise water-soluble polymers other than polyalkenoate, such as HEMA and other co-polymerizing methacrylate-modified polycarboxylic acids, which are catalyzed by photoactivation. Other hybrid dental composites may be modified to include polymerizable tertiary amines, catalyzed by reaction with peroxides.

Synthetic dental composites are increasingly used more often for dental procedures, such as restoration, reconstruction and repair, for example, fillings, crowns, bridges, dentures, orthodontic appliances, retainers, cements, posts and ancillary parts for dental implants to name a few. Most common, synthetic dental composites are used for anterior Class III and Class V reconstructions, for smaller size Class I and Class II molar reconstructions, for color-matching of cosmetic veneers, and for cementing of crowns and overlays. Nonetheless certain disadvantages of these materials have been noted. For example, the trace amounts of unconverted monomers and/or catalyst that may remain within the composite and, if subsequently absorbed systemically in humans, may be potentially physiologically harmful.

Most common, dental composites are used for reconstructions, color-matching, and cementing of crowns and overlays. Nonetheless, dental composites maintain certain disadvantages. For example, these composites tend to wear more rapidly. Perhaps the most significant disadvantage associated with dental composites is that they have a low resistance to disturbances such as cracks, breaks, fractures, splits, fissures, and gaps to name a few. Even relatively minor surface disturbances within the composite may progressively widen and expand, eventually resulting in partial or complete damage of the dental composite.

This low resistance to disturbances is also correlated with the proportional volume of the amount of synthetic composite required, or the lesser fraction of intact enamel and dentinal tooth material that remains available, prior to reconstruction, restoration or repair. It is well established from studies of the "cracked tooth syndrome" that once a damaging fracture has occurred, tooth loss may be almost inevitable, especially for carious teeth that have been previously filled. An improved synthetic dental composite having greater resistance to fracture would be significantly advantageous.

Synthetic composites having self-healing characteristics are known in the art, as illustrated for example in U.S. Pat. Nos. 6,518,330 and 6,858,659, describing self-repair of a polyester material containing unreacted amounts of dicyclopentadiene ("DCPD") monomer stored within a polyester matrix resin, as sequestered within polyoxymethyleneurea ("PMU") microcapsules. From a fracturing mechanical stress sufficient to cause rupturing of one or more microcapsule, the monomer is reactively released. As the monomer contacts the polyester matrix, a polymerization occurs. The in situ polymerization occurs as a result of a ruthenium-based Grubbs catalyst or Schrock catalyst, which may be incorporated into the matrix. Alternatively, the catalyst may be stored within a fraction of separately prepared microcapsules, or may be contained within the same material comprising the microcapsule outer wall.

Although a composite having self-healing characteristics is known in the art, there is still a demand for improved dental restorative formulations having self-healing characteristics, or the ability to automatically correct any disturbances, occurring in the composite as well as methods of making such restorative formulations. The present invention satisfies this demand.

SUMMARY OF THE INVENTION

The present invention is directed to dental restorative formulations having self-healing characteristics as a composite, and methods of making such restorative formulations.

Dental composites are formed from the polymerization of a restorative formulation. Typically, a restorative formulation comprises a resin matrix or dental material, a filler material such as silica, an initiator to begin the polymerization reaction of the dental materials when external energy such as light or heat is applied to the formulation and a catalyst to control polymerization speed. When a restorative formulation is applied, for example directly to a tooth, external energy is applied to polymerize the restorative formulation forming a composite.

A problem with dental composites is that they may be susceptible to disturbances. Disturbances include, for example, cracks, discontinuities, breaks, fractures, splits, fissures, and gaps to name a few.

The present invention solves the problem of disturbances occurring in composites by incorporating additives in dental restorative formulations to provide "self-healing" characteristics. Therefore, when disturbances occur in a composite, the composite repairs, regenerates, or reconstructs itself such that the function, integrity and morphology of the composite is brought back to an original or almost original condition.

Dental composites can be used to repair, regenerate or reconstruct a variety of dental structures such as fillings, crowns, bridges, dentures, orthodontic appliances, retainers, cements, posts and ancillary parts for dental implants. The present invention contemplates dental restorative formulations that include radicals, or free radicals, that take part in a chemical reaction to result in self-healing dental composites.

The present invention includes dental restorative formulations comprising a resin matrix or dental material with a continuous phase, wherein the dental material includes two additional additives. The first additive and second additive are stored in the continuous phase of the dental material. The dental material is one or more monomers as discussed below.

The first additive comprises a first capsule that includes a radical initiator. The second additive comprises a second capsule that includes one or more monomers and a radical accelerator. In one embodiment, it is contemplated that the first capsule and the second capsule account for about 1-15 wt % of the dental restorative formulation. The dental restorative formulation is applied and polymerized to form a composite. When a disturbance occurs in the composite, the capsules rupture so that the radical accelerator of the second capsule decomposes the radical initiator of the first capsule in order to polymerize the one or more monomers of the second capsule thereby, healing the dental composite. The radical accelerator controls the rate of decomposition of the radical initiator.

For purposes of this application, a resin matrix or dental material used for dental restorative formulations may include any combination of one or more monomers. Monomers include synthetic monomers and natural monomers. Synthetic monomers include acrylic monomers as well as hydrocarbons such as ethene as well as acrylic acid, methyl methacrylate, styrene, and acrylamide. Natural monomers include, for example, amino acids and glucose.

Dental materials according to the present invention and the one or more monomers of the second capsule of the second component may include one or more selected from the group of: 2,2-bis[4-(2-hydroxy-3-methacryloyloxypropoxy)phenyl]propane ("Bis-GMA"), dimethacryloxyethyl 2,2,4-trimethylhexamethylene diurethane ("UDMA"), and 1,6-bis-[2-methacryloxy-ethoxycarbonylamino]-2,2,4-trimethylhexane ("UEDMA"), triethyleneglycol dimethacrylate ("TEGDMA"), polyethylene glycol dimethacrylate ("PEGDMA"), glyceroldimethacrylate ("GDM"), methacryloyloxyethyl maleate ("MEMA"), diethyleneglycol dimethacrylate ("DEGDMA"), hexanediol dimethacrylate ("HDMA"), hexanediol diacrylate ("HDDA"), trimethylolpropanetriacrylate ("TMPTA"), trimethylolpropanetrimethacrylate ("TMPTMA"), ethoxylated trimethylolpropanetriacrylate ("EOTMPTA"), hydroxyethyl methacrylate ("HEMA") and ethoxylated bisphenol A dimethacrylate ("EBPADMA"), isopropyl methacrylate; n-hexyl acrylate; stearyl acrylate; diallyl phthalate; divinyl succinate; divinyl adipate; divinyl phthalate; allyl acrylate; glycerol triacrylate; ethyleneglycol diacrylate; 1,3-propanediol di(meth)acrylate; decanediol dimethacrylate; 1,12-dodecanediol di(meth)acrylate; trimethylolpropane mono- or di-(meth)acrylate; trimethylolpropane triacrylate; butanediol di(meth)acrylate; 1,2,4-butanetriol trimethacrylate; 1,4-cyclohexanediol diacrylate; pentaerythritol tetra(meth)acrylate; sorbitol mono-, di-, tri-, tetra-, or penta-(meth)acrylate; sorbitol hexa-(meth)acrylate; tetrahydrofurfuryl(meth)acrylate; bis[1-(2-acryloxy)]-p-ethoxyphenyldimethylmethane; bis[1-(3-acryloxy-2-hydroxy)]-p-propoxyphenyldimethylmethane; 2,2,4-trimethylhexamethylene diisocyanate; tris-hydroxyethyl-isocyanurate trimethacrylate, glycerol phosphate monomethacrylates; glycerol phosphate dimethacrylates; hydroxyethyl methacrylate phosphates; 2-hydroxypropyl(meth)acrylate; citric acid di- or tri-methacrylates; fluoropolymer-functional (meth)acrylates; poly (meth)acrylated polymaleic acid; poly(meth)acrylated polycarboxyl-polyphosphonic acid; poly(meth)acrylated polychlorophosphoric acid; poly(meth)acrylated polysulfonic acid; poly(meth)acrylated polyboric acid; polymerizable bisphosphonic acids, and siloxane-functional (meth) acrylate polysiloxanes, defined as products resulting from hydrolytic polycondensation of one or more of the following silanes: bis[2-(2-(methacryloyl oxyethoxycarbonyl)ethyl)]-3¬triethoxysily-lpropyl amine, bis[2-(2(1)-(methacryloyloxypropoxycarbonyl)ethyl)]-3-triet-hoxysilylpropyl amine, 1,3(2)-dimethacryloyloxypropyl-[3-(3-triethoxysilyl-propyl)aminocarbonyl]propionate, 1,3(2)-dimethacryloyloxypropyl-[4-(3-trie-thoxysilyl propyl)aminocarbonyl]butyrate, 1,3(2)-dimethacryloyloxypropyl-[4-(3-triethoxysilylpropyl)-N-¬ethylaminocarbonyl]butyrate, 3-[1,3(2)-dimethacryloyl oxypropyl)-2(3)-oxycarbonylamido]¬propyltriethoxysilane, glycerol phosphate monomethacrylates, glycerol phosphate dimethacrylates, hydroxyethyl methacrylate phosphates, citric acid di- or trimethacrylates, poly(meth)acrylated oligomaleic acid, poly (meth)acrylated polymaleic acid, poly(meth)acrylated poly (meth)acrylic acid, poly(meth)acrylated polycarboxylpolyphosphonic acid, poly(meth)acrylated polychlorophosphoric acid, poly(meth)acrylated polysulfonic acid, poly(meth)acrylated polyboric acid and polymerizable bisphosphonic acids. It is contemplated that any formulation for a dental composite may include multiple monomers, including any combination of the foregoing.

Initiators initiate a reaction that polymerizes one or more monomers. Polymerization is either step-growth or chain-growth. Step-growth polymerization occurs when polymers are formed by the stepwise reaction between functional groups of monomers. Chain-growth polymerization, such as radical polymerization, occurs when polymers are formed by the addition of monomer molecules one at a time. According to the present invention, radical initiators, or radical polymerization initiators, are one or more substances such as azo compounds, inorganic peroxides, acetophenone, benzil/benzoin, redox, ylide, benzophenone, thioxanthones and organic peroxides that promote radical polymerization reactions. More specific examples of radical initiators include benzoyl peroxide or methyl ethyl ketone peroxide.

An accelerator is a substance that speeds up (accelerates) a chemical reaction. According to the present invention, a radical accelerator decomposes the radical initiator at a controlled rate. The controlled decomposition of the radical initiator initiates polymerization of one or more monomers thereby healing the dental composite. Additionally, a radical accelerator according to the present invention can decompose the radical initiator independent of temperature.

Common radical accelerators include one or more selected from the group of: organic peroxides such as aromatic, acyclic and cyclic aliphatic, and aliphatic-aromatic primary, secondary and tertiary amines. More specific examples include one or more selected from the group of: dimethyl amine, trimethyl amine, ethyl amine, diethyl amine, triethyl amine, n-propyl amine, di-n-propyl amine, tri-n-propyl amine, isopropyl amine, diisopropyl amine, triisopropyl amine, n-butyl amine, isobutyl amine, t-butyl amine, di-n-butyl amine, diisobutyl amine, tri-isobutyl amine, pentyl amine, isopentyl amine, diisopentyl amine, hexyl amine, octyl amine, dodecyl amine, lauryl amine, stearyl amine, aminoethanol, diethanol amine, triethanol amine, aminohexanol, ethoxy aminoethane, dimethyl-(2-chloroethyl)amine, 2-ethylhexyl amine, bis-(2-chloroethyl)amine, 2-ethylhexyl amine, bis-(2-ethylhexyl) amine, N-methyl stearylamine, dialkyl amines, ethylene diamine, N.N'-dimethyl ethylene diamine, tetramethyl ethylene diamine, diethylene triamine, permethyl diethylene triamine, triethylene tetramine, tetraethylene pentamine, 1.2-diaminopropane, di-propylene triamine, tripropylene tetramine, 1.4-diamino butane, 1.6-diamino hexane, 4-amino-1-diethyl aminopentane, 2.5-diamino-2.5-dimethyl hexane, trimethyl hexamethylene diamine, N.N-dimethyl aminoethanol, 2-(2-diethylamino ethoxy)ethanol, bis-(2-hydroxyethyl)-oleyl amine, tris-[2-(2-hydroxy-ethoxy)-ethyl] amine, 3-amino-1-propanol, methyl-(3-aminopropyl)ether, ethyl-(3-aminopropyl)ether, 1.4-butane diol-bis(3-aminopropyl ether), 3-dimethylamino-1-propanol, 1-amino-2-propanol, 1-diethylamino-2-propanol, diisopropanol amine, methyl-bis-(2-hydroxypropyl)-amine, tris-(2-hydroxypropyl) amine, 4-amino-2-butanol, 2-amino-2-methylpropanol, 2-amino-2-methyl-propanediol, 2-amino-2-hydroxymethyl-propanediol, 5-diethylamino-2-pentanone, 3-methylaminopropionic acid nitrile, 6-aminohexanoic acid, 11-aminoundecanoic acid, 6-aminohexanoic acid ethyl ester, 11-aminohexanoic acid isopropyl ester, cyclohexyl amine, N-methylcyclohexyl amine, N.N-dimethylcyclohexyl amine, dicyclohexyl amine, N-ethylcyclohexyl amine, N-(2-hydroxyethyl)-cyclohexyl amine, N.N-bis-(2-hydroxyethyl)-cyclohexyl amine, N-(3-aminopropyl)-cyclohexyl amine, aminomethyl cyclohexane, hexahydro toluidine, hexahydro benzylamine, aniline, N-methyl aniline, N.N-dimethyl aniline, N.N-diethyl aniline, N.N-di-propyl aniline, isobutyl aniline, toluidines, diphenyl amine, hydroxyethyl aniline, bis-(hydroxyethyl)aniline, chloro-aniline, aminophenols, aminobenzoic acids and their esters, benzyl amine, dibenzyl amine, tribenzyl amine, methyldibenzyl amine, α-phenylethyl amine, xylidine, diisopropyl aniline, dodecyl aniline, amino naphthalene, N-methyl aminonaphthalene, N.N-dimethyl aminonaphthalene, N.N-dibenzyl naphthalene, diamino cyclohexane, 4.4'-diamino-dicyclohexyl methane, diamino-dimethyl-dicyclohexyl methane, phenylene diamine, xylylene diamine, diamino biphenyl, naphthalene diamines, toluidines, benzidines, 2.2-bis-(aminophenyl)-propane, amino anisoles, amino-thiophenols, aminodiphenyl ethers, amino cresols, morpholine, N-methyl morpholine, N-phenyl morpholine, hydroxyethyl morpholine, N-methylpyrrolidine, pyrrolidine, piperidine, hydroxyethyl piperidine, pyrrols, pyridines, chinolines, indoles, indolenines, carbazoles, pyrazoles, imidazoles, thiazoles, pyrimidines, chinoxalines, amino morpholine, dimorpholine ethane, [2,2,2]-diazabicyclo octane, and N,N-dimethyl-p-toluidine.

Capsules, or microspheres, encapsulate the radical accelerator, radical initiator, and one or more monomers according to the present invention. More specifically, the first capsule encapsulates a radical initiator, which may be encapsulated as a liquid element or an element dissolved in a liquid. The second capsule encapsulates a radical accelerator and one or more monomers.

Methods for constructing capsules or microspheres may by physical or chemical. Physical methods of manufacturing include pan coating, air-suspension coating, centrifugal extrusion, vibrational nozzle and spray-drying. Chemical methods of manufacturing include polymerization such as interfacial polymerization, in-situ polymerization and matrix polymerization. In interfacial polymerization, at least two monomers are dissolved separately in immiscible liquids. Upon interface between the liquids, rapid reaction occurs creating a thin shell or wall of the microsphere. In-situ polymerization is the direct polymerization of a single monomer carried out on the particle surface. Matrix polymerization, a core material is imbedded during formation of the microsphere. Capsules might also be constructed by using sol-gel techniques, by aqueous or organic solution precipitation synthesis methods, complex coacervation, interfacial polymerization, or by other methods known in the art.

As mentioned above, when a disturbance occurs in the dental composite, the capsules rupture so that the radical accelerator of the second capsule decomposes the radical initiator of the first capsule to polymerize the one or more monomers of the second capsule thereby healing the dental composite.

A primary object of the present invention is to provide dental restorative formulations with self-healing characteristics, or capability to autonomically resolve disturbances, occurring in composites polymerized from the restorative formulations.

Another object of the present invention is to provide a dental restorative formulation that polymerizes to a composite that wears slowly compared to existing composites and has a greater resistance to disturbances.

Another object of the present invention is to provide a dental restorative formulation that can be applied as a monomer directly to the teeth of the patient.

Another object of the present invention is to provide a dental restorative formulation that is biocompatible.

It will of course be understood that the aspects and objectives of the invention are various, and need not be all present in any given embodiment of the invention. The features, advantages and accomplishments of the invention will be further appreciated and understood upon consideration of the following detailed description of embodiments of the invention.

BRIEF DESCRIPTION OF THE DRAWINGS

FIG. 1 illustrates an embodiment of a dental restorative formulation according to the present invention.

DETAILED DESCRIPTION

This application incorporates by reference the entire subject matter of U.S. patent application Ser. No. 11/809,248 filed May 31, 2007.

As shown in FIG. 1, a dental restorative formulation 100 includes a first additive 110 and a second additive 120 incorporated into the continuous phase of a resin matrix, a or dental material 130. The first additive 110 includes a first capsule 115 and the second additive 120 includes a second capsule 125. It is contemplated that the first capsule and the second capsule account for about 1-15 wt % of the dental restorative formulation.

For purposes of this application, a dental material 130 is one or more monomers selected from the group of: 2,2-bis[4-(2-hydroxy-3-methacryloyloxypropoxy)phenyl]propane ("Bis-GMA"), dimethacryloxyethyl 2,2,4-trimethylhexamethylene diurethane ("UDMA"), and 1,6-bis[2-methacryloxy-ethoxycarbonylamino]-2,2,4-trimethylhexane ("UEDMA"), triethyleneglycol dimethacrylate ("TEGDMA"), polyethylene glycol dimethacrylate ("PEGDMA"), glyceroldimethacrylate ("GDM"), methacryloyloxyethyl maleate ("MEMA"), diethyleneglycol dimethacrylate ("DEGDMA"), hexanediol dimethacrylate ("HDMA"), hexanediol diacrylate ("HDDA"), trimethylolpropanetriacrylate ("TMPTA"), trimethylolpropanetrimethacrylate ("TMPTMA"), ethoxylated trimethylolpropanetriacrylate ("EOTMPTA"), hydroxyethyl methacrylate ("HEMA") and ethoxylated bisphenol A dimethacrylate ("EBPADMA"), isopropyl methacrylate; n-hexyl acrylate; stearyl acrylate; diallyl phthalate; divinyl succinate; divinyl adipate; divinyl phthalate; allyl acrylate; glycerol triacrylate; ethyleneglycol diacrylate; 1,3-propanediol di(meth)acrylate; decanediol dimethacrylate; 1,12-dodecanediol di(meth)acrylate; trimethylolpropane mono- or di-(meth)acrylate; trimethylolpropane triacrylate; butanediol di(meth)acrylate; 1,2,4-butanetriol trimethacrylate; 1,4-cyclohexanediol diacrylate; pentaerythritol tetra(meth)acrylate; sorbitol mono-, di-, tri-, tetra-, or penta-(meth)acrylate; sorbitol hexa-(meth)acrylate; tetrahydrofurfuryl(meth)acrylate; bis[1-(2-acryloxy)]-p-ethoxyphenyldimethylmethane; bis[1-(3-acryloxy-2-hydroxy)]-p-propoxyphenyldimethylmethane; 2,2,4-trimethylhexamethylene diisocyanate; tris-hydroxyethylisocyanurate trimethacrylate, glycerol phosphate monomethacrylates; glycerol phosphate dimethacrylates; hydroxyethyl methacrylate phosphates; 2-hydroxypropyl (meth)acrylate; citric acid di- or tri-methacrylates; fluoropolymer-functional (meth)acrylates; poly(meth)acrylated polymaleic acid; poly(meth)acrylated polycarboxyl-polyphosphonic acid; poly(meth)acrylated polychlorophosphoric acid; poly(meth)acrylated polysulfonic acid; poly(meth)acrylated polyboric acid; polymerizable bisphosphonic acids, and siloxane-functional (meth)acrylate polysiloxanes, defined as products resulting from hydrolytic polycondensation of one or more of the following silanes: bis[2-(2-(methacryloyl oxyethoxycarbonyl)ethyl)]-3-¬ triethoxysily-lpropyl amine, bis[2-(2(1)-(methacryloyloxypropoxycarbonyl) ethyl)]-3-triet-hoxysilylpropyl amine, 1,3(2)-dimethacryloyloxypropyl-[3-(3-triethoxysilyl-propyl) aminocarbonyl]propionate, 1,3(2)-dimethacryloyloxypropyl-[4-(3-trie-thoxysilyl propyl) aminocarbonyl]butyrate, 1,3(2)-dimethacryloyloxypropyl-[4-(3-triethoxysilylpropyl)-N-¬ ethylaminocarbonyl] butyrate, 3-[1,3(2)-dimethacryloyl oxypropyl)-2(3)-oxycarbonylamido]¬ propyltriethoxysilane, glycerol phosphate monomethacrylates, glycerol phosphate dimethacrylates, hydroxyethyl methacrylate phosphates, citric acid di- or tri-methacrylates, poly(meth)acrylated oligomaleic acid, poly(meth)acrylated polymaleic acid, poly (meth)acrylated poly(meth)acrylic acid, poly(meth)acrylated polycarboxyl-polyphosphonic acid, poly(meth)acrylated polychlorophosphoric acid, poly(meth)acrylated polysulfonic acid, poly(meth)acrylated polyboric acid and polymerizable bisphosphonic acids. It is contemplated that any formulation for a dental composite may include multiple monomers, including any combination of the foregoing.

The first additive 110 incorporated into the continuous phase of the dental material 130 comprises a first capsule 115 including a radical initiator 117. In one embodiment, the radical initiator 117 is an organic peroxide initiator, more specifically, benzoyl peroxide. It is also contemplated that the radical initiator 117 may include substances such as azo compounds, inorganic peroxides, acetophenone, benzil/benzoin, redox, ylide, benzophenone, thioxanthones and organic peroxides including methyl ethyl ketone peroxide.

The second additive 120 incorporated into the continuous phase of the dental material 130 comprises a second capsule 125 that includes one or more monomers 127 and a radical accelerator 129.

Again, the one or more monomers 127 of the second capsule 125 are one or more selected from the group of: 2,2-bis [4-(2-hydroxy-3-methacryloyloxypropoxy)phenyl]propane ("Bis-GMA"), dimethacryloxyethyl 2,2,4-trimethylhexamethylene diurethane ("UDMA"), and 1,6-bis-[2-methacryloxy-ethoxycarbonylamino]-2,2,4-trimethylhexane ("UEDMA"), triethyleneglycol dimethacrylate ("TEGDMA"), polyethylene glycol dimethacrylate ("PEGDMA"), glyceroldimethacrylate ("GDM"), methacryloyloxyethyl maleate ("MEMA"), diethyleneglycol dimethacrylate ("DEGDMA"), hexanediol dimethacrylate ("HDMA"), hexanediol diacrylate ("HDDA"), trimethylolpropanetriacrylate ("TMPTA"), trimethylolpropanetrimethacrylate ("TMPTMA"), ethoxylated trimethylolpropanetriacrylate ("EOTMPTA"), hydroxyethyl methacrylate ("HEMA") and ethoxylated bisphenol A dimethacrylate ("EBPADMA"), isopropyl methacrylate; n-hexyl acrylate; stearyl acrylate; diallyl phthalate; divinyl succinate; divinyl adipate; divinyl phthalate; allyl acrylate; glycerol triacrylate; ethyleneglycol diacrylate; 1,3-propanediol di(meth)acrylate; decanediol dimethacrylate; 1,12-dodecanediol di(meth)acrylate; trimethylolpropane mono- or di-(meth)acrylate; trimethylolpropane triacrylate; butanediol di(meth)acrylate; 1,2,4-butanetriol trimethacrylate; 1,4-cyclohexanediol diacrylate; pentaerythritol tetra(meth)acrylate; sorbitol mono-, di-, tri-, tetra-, or penta-(meth)acrylate; sorbitol hexa-(meth)acrylate; tetrahydrofurfuryl(meth)acrylate; bis[1-(2-acryloxy)]-p-ethoxyphenyldimethylmethane; bis[1-(3-acryloxy-2-hydroxy)]-p-propoxyphenyldimethylmethane; 2,2,4-trimethylhexamethylene diisocyanate; tris-hydroxyethyl-isocyanurate trimethacrylate, glycerol phosphate monomethacrylates; glycerol phosphate dimethacrylates; hydroxyethyl methacrylate phosphates; 2-hydroxypropyl (meth)acrylate; citric acid di- or tri-methacrylates; fluoropolymer-functional (meth)acrylates; poly(meth)acrylated polymaleic acid; poly(meth)acrylated polycarboxyl-polyphosphonic acid; poly(meth)acrylated polychlorophosphoric acid; poly(meth)acrylated polysulfonic acid; poly(meth)acrylated polyboric acid; polymerizable bisphosphonic acids, and siloxane-functional (meth)acrylate polysiloxanes, defined as products resulting from hydrolytic polycondensation of one or more of the following silanes: bis[2-(2-(methacryloyl oxyethoxycarbonyl)ethyl)]-3-¬ triethoxysily-lpropyl amine, bis[2-(2(1)-(methacryloyloxypropoxycarbonyl) ethyl)]-3-triet-hoxysilylpropyl amine, 1,3(2)-dimethacryloyloxypropyl-[3-(3-triethoxysilyl-propyl) aminocarbonyl]propionate, 1,3(2)-dimethacryloyloxypropyl-[4-(3-trie-thoxysilyl propyl) aminocarbonyl]butyrate, 1,3(2)-dimethacryloyloxypropyl-[4-(3-triethoxysilylpropyl)-N-¬ ethylaminocarbonyl] butyrate, 3-[1,3(2)-dimethacryloyl oxypropyl)-2(3)-oxycarbonylamido]¬ propyltriethoxysilane, glycerol phosphate monomethacrylates, glycerol phosphate dimethacrylates, hydroxyethyl methacrylate phosphates, citric acid di- or tri-methacrylates, poly(meth)acrylated oligomaleic acid, poly(meth)acrylated polymaleic acid, poly (meth)acrylated poly(meth)acrylic acid, poly(meth)acrylated polycarboxyl-polyphosphonic acid, poly(meth)acrylated polychlorophosphoric acid, poly(meth)acrylated polysulfonic acid, poly(meth)acrylated polyboric acid and polymerizable bisphosphonic acids. It is contemplated that any formulation for a dental composite may include multiple monomers, including any combination of the foregoing.

According to the present invention, the radical accelerator 129 is specifically an accelerator for organic peroxide decomposition, for example, benzoyl peroxide decomposition. In one embodiment, the radical accelerator 129 is N,N-dimethyl-p-toluidine, but it is contemplated that the radical accelerator 129 may also be one or more amines selected from the group comprising of: dimethyl amine, trimethyl amine, ethyl amine, diethyl amine, triethyl amine, n-propyl amine, di-n-propyl amine, tri-n-propyl amine, isopropyl amine, diisopropyl amine, triisopropyl amine, n-butyl amine, isobutyl amine, t-butyl amine, di-n-butyl amine, diisobutyl amine, tri-isobutyl amine, pentyl amine, isopentyl amine, diisopentyl amine, hexyl amine, octyl amine, dodecyl amine, lauryl amine, stearyl amine, aminoethanol, diethanol amine, triethanol amine, aminohexanol, ethoxy aminoethane, dimethyl-(2-chloroethyl) amine, 2-ethylhexyl amine, bis-(2-chloroethyl) amine, 2-ethylhexyl amine, bis-(2-ethylhexyl) amine, N-methyl stearylamine, dialkyl amines, ethylene diamine, N,N'-dimethyl ethylene diamine, tetramethyl ethylene diamine, diethylene triamine, permethyl diethylene triamine, triethylene tetramine, tetraethylene pentamine, 1.2-diaminopropane, di-propylene triamine, tripropylene tetramine, 1.4-diamino butane, 1.6-diamino hexane, 4-amino-1-diethyl aminopentane, 2.5-diamino-2.5-dimethyl hexane, trimethyl hexamethylene diamine, N.N-dimethyl aminoethanol, 2-(2-diethylamino ethoxy)ethanol, bis-(2-hydroxyethyl)-oleyl amine, tris-[2-(2-hydroxy-ethoxy)-ethyl]amine, 3-amino-1-propanol, methyl-(3-aminopropyl)ether, ethyl-(3-aminopropyl) ether, 1.4-butane diol-bis(3-aminopropyl ether), 3-dimethylamino-1-propanol, 1-amino-2-propanol, 1-diethylamino-2-propanol, diisopropanol amine, methyl-bis-(2-hydroxypropyl)-amine, tris-(2-hydroxypropyl)amine, 4-amino-2-butanol, 2-amino-2-methylpropanol, 2-amino-2-methyl-propanediol, 2-amino-2-hydroxymethylpropanediol, 5-diethylamino-2-pentanone, 3-methylaminopropionic acid nitrile, 6-aminohexanoic acid, 11-aminoundecanoic acid, 6-aminohexanoic acid ethyl ester, 11-aminohexanoic acid isopropyl ester, cyclohexyl amine, N-methylcyclohexyl amine, N,N-dimethylcyclohexyl amine, dicyclohexyl amine, N-ethylcyclohexyl amine, N-(2-hydroxyethyl)-cyclohexyl amine, N,N-bis-(2-hydroxyethyl)-cyclohexyl amine, N-(3-aminopropyl)-cyclohexyl amine, aminomethyl cyclohexane, hexahydro toluidine, hexahydro benzylamine, aniline, N-methyl aniline, N,N-dimethyl aniline, N,N-diethyl aniline, N,N-di-propyl aniline, isobutyl aniline, toluidines, diphenyl amine, hydroxyethyl aniline, bis-(hydroxyethyl)aniline, chloro-aniline, aminophenols, aminobenzoic acids and their esters, benzyl amine, dibenzyl amine, tribenzyl amine, methyldibenzyl amine, α-phenylethyl amine, xylidine, diisopropyl aniline, dodecyl aniline, amino naphthalene, N-methyl aminonaphthalene, N,N-dimethyl aminonaphthalene, N,N-dibenzyl naphthalene, diamino cyclohexane, 4.4'-diamino-dicyclohexyl methane, diamino-dimethyl-dicyclohexyl methane, phenylene diamine, xylylene diamine, diamino biphenyl, naphthalene diamines, toluidines, benzidines, 2.2-bis-(aminophenyl)-propane, amino anisoles, amino-thiophenols, aminodiphenyl ethers, amino cresols, morpholine, N-methyl morpholine, N-phenyl morpholine, hydroxyethyl morpholine, N-methylpyrrolidine, pyrrolidine, piperidine, hydroxyethyl piperidine, pyrrols, pyridines, chinolines, indoles, indolenines, carbazoles, pyrazoles, imidazoles, thiazoles, pyrimidines, chinoxalines, amino morpholine, dimorpholine ethane, [2,2,2]-diazabicyclo octane, and N,N-dimethyl-p-toluidine.

The dental restorative formulation 100 is applied and polymerized to form a composite. When a disturbance occurs in the dental composite, the first capsule 115 and second capsule 125 rupture releasing the contents of the capsules 115, 125, for example, the radical initiator 117, specifically benzoyl peroxide initiator, of the first capsule 115 is released and the radical accelerator 129, specifically N,N-dimethyl-p-toluidine accelerator, of the second capsule 125 is released along with the one or more monomers 127. The N,N-dimethyl-p-toluidine accelerator controls the rate of decomposition of the benzoyl peroxide initiator to polymerize the one or more monomers thereby healing the dental composite.

Those of ordinary skill in the art will appreciate that the various derivates of dental materials, radical initiators, radical accelerators and one or more monomers discussed herein can be utilized with embodiments in accordance with the present invention. The invention has been described with reference to a certain described embodiment. Obviously, modifications and alterations will occur to others upon reading and understanding the preceding detailed description. Indeed, it is contemplated that radical initiators and radical accelerators for use in accordance with the present invention could preferably be substituted in a number of ways. It is intended that the invention be construed as including all such modifications and alterations insofar as they come within the scope of the appended claims or the equivalents thereof.

What is claimed is:

1. A dental restorative formulation, comprising:
   a first capsule consisting of a radical initiator within said first capsule; and
   a second capsule consisting of one or more monomers and a radical accelerator within said second capsule, the dental restorative formulation is polymerized to form a composite and upon the occurrence of a disturbance in the composite said first capsule and said second capsule rupture such that said radical accelerator of said second capsule decomposes said radical initiator of said first capsule to polymerize said one or more monomers of said second capsule thereby healing the composite.

2. The dental restorative formulation of claim 1, wherein said radical initiator is an organic peroxide initiator.

3. The dental restorative formulation of claim 1, wherein said radical initiator is benzoyl peroxide.

4. The dental restorative formulation of claim 1, wherein said one or more monomers is acrylic monomers.

5. The dental restorative formulation of claim 1, wherein said one or more monomers is triethyleneglycol dimethacrylate ("TEGDMA").

6. The dental restorative formulation of claim 1, wherein said one or more monomers is 2,2-bis[4-(2-hydroxy-3-methacryloyloxypropoxy)phenyl]propane ("Bis-GMA").

7. The dental restorative formulation of claim 1, wherein said one or more monomers is 2,2,4-trimethylhexamethylene diurethane ("UDMA").

8. The dental restorative formulation of claim 1, wherein said radical accelerator is N,N-dimethyl-p-toluidine.

9. The dental restorative formulation of claim 1, wherein said one or more monomers are selected from the group consisting of: 2,2-bis[4-(2-hydroxy-3-methacryloyloxypropoxy) phenyl]propane ("Bis-GMA"), dimethacryloxyethyl 2,2,4-trimethylhexamethylene diurethane ("UDMA"), and 1,6-bis-[2-methacryloxy-ethoxycarbonylamino]-2,2,4-trimethylhexane ("UEDMA"), triethyleneglycol dimethacrylate ("TEGDMA"), polyethylene glycol dimethacrylate ("PEGDMA"), glyceroldimethacrylate ("GDM"), methacryloyloxyethyl maleate ("MEMA"), diethyleneglycol dimethacrylate ("DEGDMA"), hexanediol dimethacrylate ("HDMA"), hexanediol diacrylate ("HDDA"), trimethylolpropanetriacrylate ("TMPTA"), trimethylolpropanetrimethacrylate ("TMPTMA"), ethoxylated trimethylolpropanetriacrylate ("EOTMPTA"), hydroxyethyl methacrylate ("HEMA") and ethoxylated bisphenol A dimethacrylate ("EBPADMA"), isopropyl methacrylate; n-hexyl acrylate; stearyl acrylate; diallyl phthalate; divinyl succinate; divinyl adipate: divinyl phthalate; allyl acrylate; glycerol triacrylate; ethyleneglycol diacrylate; 1,3-propanediol di(meth)acrylate; decanediol dimethacrylate; 1,12-dodecanediol di(meth)acrylate; trimethylolpropane mono- or di-(meth)acrylate; trimethylolpropane triacrylate; butanediol di(meth)acrylate; 1,2,4-butanetriol trimethacrylate: 1,4-cyclohexanediol diacrylate; pentaerythritol tetra(meth)acrylate; sorbitol mono-, di-, tri-, tetra-, or penta-(meth)acrylate; sorbitol hexa-(meth)acrylate; tetrahydrofurfuiryl (meth)acrylate; bis[1-(2-acryloxy)]-p-ethoxyphenyldimethylmethane; bis[1-(3-acryloxy-2-hydroxy)]-p-propoxyphenyldimethylmethane; 2,2,4-trimethylhexamethylene diisocyanate; tris-hydroxyethyl-isocyanurate trimethacrylate, glycerol phosphate monomethacrylates; glycerol phosphate dimethacrylates; hydroxyethyl methacrylate phosphates; 2-hydroxypropyl (meth)acrylate; citric acid di- or tri-methacrylates; fluoropolymer-functional (meth)acrylates; poly(meth)acrylated polymaleic acid; poly(meth)acrylated polycarboxyl-polyphosphonic acid; poly(meth)acrylated polychlorophosphoric acid; poly(meth)acrylated polysulfonic acid; poly(meth)acrylated polyboric acid; polymerizable bisphosphonic acids, and siloxane-functional (meth)acrylate polysiloxanes, defined as products resulting from hydrolytic polycondensation of one or more of the following silanes: bis[2-(2-(methacryloyl oxyethoxycarbonyl)ethyl)]-3-triethoxysily-lpropyl amine, bis[2-(2(1)-(methacryloyloxypropoxycarbonyl) ethyl)]-3-triet-hoxysilylpropyl amine, 1,3(2)-dimethacryloyloxypropyl-[3-(3-triethoxysilyl-propyl)aminocarbonyl]propionate, 1,3(2)-dimethacryloyloxypropyl-[4-(3-triethoxysilylpropyl)aminocarbonyl]butyrate, 1,3(2)-dimethacryloyloxypropyl-[-4-(3-triethoxysilylpropyl)-N-ethylaminocarbonyl]butyrate, 3-[1,3(2)-dimethacryloyl oxypropyl]-2(3)-oxycarbonylamido]-propyltriethoxysilane, glycerol phosphate monomethacrylates, glycerol phosphate dimethacrylates, hydroxyethyl methacrylate phosphates, citric acid di- or tri-methacrylates, poly(meth)acrylated oligomaleic acid, poly(meth)acrylated polymaleic acid, poly (meth)acrylated poly(meth)acrylic acid, poly(meth)acrylated polycarboxyl-polyphosphonic acid, poly(meth)acrylated polychlorophosphoric acid, poly(meth)acrylated polysulfonic acid, poly(meth)acrylated polyboric acid and polymerizable bisphosphonic acids.

10. The dental restorative formulation of claim 1, wherein said radical accelerator includes one or more amines selected from the group consisting of: dimethyl amine, trimethyl amine, ethyl amine, diethyl amine, triethyl amine, n-propyl amine, di-n-propyl amine, tri-n-propyl amine, isopropyl amine, diisopropyl amine, triisopropyl amine, n-butyl amine, isobutyl amine, t-butyl amine, di-n-butyl amine, diisobutyl amine, tri-isobutyl amine, pentyl amine, isopentyl amine, diisopentyl amine, hexyl amine, octyl amine, dodecyl amine, lauryl amine, stearyl amine, aminoethanol, diethanol amine, triethanol amine, aminohexanol, ethoxy aminoethane, dimethyl-(2-chloroethyl) amine, 2-ethylhexyl amine, bis-(2-chloroethyl) amine, 2-ethylhexyl amine, bis-(2-ethylhexyl) amine, N-methyl stearylamine, dialkyl amines, ethylene diamine, N,N'-dimethyl ethylene diamine, tetramethyl ethylene diamine, diethylene triamine, permethyl diethylene triamine, triethylene tetramine, tetraethylene pentamine, 1,2-diaminopropane, di-propylene triamine, tripropylene tetramine, 1,4-diamino butane, 1,6-diamino hexane, 4-amino-1-diethyl aminopentane, 2,5-diamino-2,5-dimethyl hexane, trimethyl hexamethylene diamine, N,N-dimethyl aminoethanol, 2-(2-diethylamino ethoxy) ethanol, bis-(2-hydroxyethyl)-oleyl amine, tris-[2-(2-hydroxy-ethoxy)-ethyl] amine, 3-amino-1-propanol, methyl-(3-aminopropyl)ether, ethyl-(3-aminopropyl)ether, 1,4-butane diol-bis(3-aminopropyl ether), 3-dimethylamino-1-propanol, 1-amino-2-propanol, 1-diethylamino-2-propanol, diisopropanol amine, methyl-bis-(2-hydroxypropyl)-amine, tris-(2-hydroxypropyl) amine, 4-amino-2-butanol, 2-amino-2-methylpropanol, 2-amino-2-methyl-propanediol, 2-amino-2-hydroxymethylpropanediol, 5-diethylamino-2-pentanone, 3-methylaminopropionic acid nitrile, 6-aminohexanoic acid, 11-aminoundecanoic acid, 6-aminohexanoic acid ethyl ester, 11-aminohexanoic acid isopropyl ester, cyclohexyl amine, N-methylcyclohexyl amine, N,N-dimethylcyclohexyl amine, dicyclohexyl amine, N-ethylcyclohexyl amine, N-(2-hydroxyethyl)-cyclohexyl amine, N,N-bis-(2-hydroxyethyl)-cyclohexyl amine, N-(3-aminopropyl)-cyclohexyl amine, aminomethyl cyclohexane, hexahydro toluidine, hexahydro benzylamine, aniline, N-methyl aniline, N,N-dimethyl aniline, N,N-diethyl aniline, N,N-di-propyl aniline, isobutyl aniline, toluidines, diphenyl amine, hydroxyethyl aniline, bis-(hydroxyethyl) aniline, chloro-aniline, aminophenols, aminobenzoic acids and their esters, benzyl amine, dibenzyl amine, tribenzyl amine, methyldibenzyl amine, a-phenylethyl amine, xylidine, diisopropyl aniline, dodecyl aniline, amino naphthalene, N-methyl aminonaphthalene, N,N-dimethyl aminonaphthalene, N,N-dibenzyl naphthalene, diamine cyclohexane, 4,4'-diamino-dicyclohexyl methane, diamino-dimethyl-dicyclohexyl methane, phenylene diamine, xylylene diamine, diamine biphenyl, naphthalene diamines, toluidines, benzidines, 2,2-bis-(aminophenyl)-propane, amino anisoles, amino-thiophenols, aminodiphenyl ethers, amino cresols, morpholine, N-methyl morpholine, N-phenyl morpholine, hydroxyethyl morpholine, N-methyl pyrrolidine, pyrrolidine, piperidine, hydroxyethyl piperidine, pyrrols, pyridines, chinolines, indoles, indolenines, carbazoles, pyrazoles, imidazoles, thiazoles, pyrimidines, chinoxalines, amino morpholine, dimorpholine ethane, [2,2,2]-diazabicyclo octane, and N,N-dimethyl-p-toluidine.

11. The dental restorative formulation of claim 1, wherein said radical initiator is one or more selected from the group consisting of: azo compounds, inorganic peroxides, acetophenone, benzil/benzoin, redox, ylide, benzophenone, thioxanthones and organic peroxides.

12. The dental restorative formulation of claim 1, wherein the said first capsule and said second capsule account for about 1-15 wt % of the dental composite.

13. A method of forming a dental composite including a dental restorative formulation, comprising the steps of:
providing a dental material;
adding a first capsule to the dental material, wherein the first capsule consists of a radical initiator within the first capsule;
introducing a second capsule to the dental material, wherein the second capsule consists of one or more monomers and a radical accelerator within the second capsule;
applying the dental material including the first capsule additive and the second capsule and
polymerizing the dental material to form a dental composite,
wherein a rupturing of the first capsule and the second capsule when a disturbance occurs in the dental composite causes the radical accelerator of the second capsule to decompose the radical initiator of the first capsule to polymerize the one or more monomers of the second capsule thereby healing the disturbance in the dental composite.

* * * * *